United States Patent [19]

Ozaki et al.

[11] Patent Number: 4,904,599

[45] Date of Patent: Feb. 27, 1990

[54] DNA FRAGMENTS CONTAINING ALKALINE CELLULASE GENE, RECOMBINANT PLASMIDS WITH SAID DNA FRAGMENTS INSERTED THEREIN, AND RECOMBINANT MICROORGANISMS

[75] Inventors: Katsuya Ozaki; Kazushi Oshino; Kenzo Koike; Susumu Ito, all of Utsunomiya; Kikuhiko Okamoto, Koshigaya, all of Japan

[73] Assignee: KAO Corporation, Tokyo, Japan

[21] Appl. No.: 109,510

[22] Filed: Oct. 19, 1987

[30] Foreign Application Priority Data

Oct. 31, 1986 [JP] Japan .................................. 61-259923

[51] Int. Cl.$^4$ .......................... C12N 9/42; C12N 7/00; C12N 15/00; C07H 15/12
[52] U.S. Cl. ............................... 435/252.33; 435/320; 435/209; 435/172.3; 435/252.31; 435/252.3; 536/27; 935/14; 935/27; 935/56; 935/60; 935/72; 935/73
[58] Field of Search ...................... 435/172.3, 209, 320, 435/252.31, 252.5; 935/29, 74; 536/27

[56] References Cited

PUBLICATIONS

Fukumori, F. et al., *J. Gen. Micro.*, 132:2329–2335, 1986.
Nakamura et al., *Eur. J. Biochem*, 164(2):317–20, 1987.
Biotechnology Advances, vol. 2, No. 2, 1984, pp. 201–216, Pergamon Press, Ltd, Oxford, GB; V. L. Seligy, Jr. et al.: "Applications of Recombinant DNA Technology to the Pulp and Paper Industry".
Agriculture and Biological Chemistry, vol. 50, No. 1, Jan. 1986, pp. 233–237, Tokyo, JP; Y. Koide et al.: "Molecular Cloning of a Cellulase Gene from *Bacillus subtilis* and its Expression in *Escherichia coli*".
Journal of Bacteriology, vol. 158, No. 2, May 1984, pp. 503–506, American Society for Microbiology; S. Nobuhiro et al.: "Molecular Cloning and Expression of Cellulase Genes of Alkalophilic Bacillus sp. strain N–4 in *Escherichia coli*".
Journal of Bacteriology, vol. 165, No. 2, Feb. 1986, pp. 612–619, American Society for Microbiology; L. M. Robson et al.: "Cloning of the *Bacillus subtilis* DLG beta–1,4–Glucanase Gene and Its Expression in *Escherichia coli* and *B. subtilis*".
Chemical Abstracts, vol. 108, 1988, p. 166, Abstract No. 32738m, Columbus, Ohio, US; T. Kudo et al.: "Alkaline Cellulase Genes from Alkalophilic Bacillus", & Iden 1987, 41(8), 26–9, abstract only.

*Primary Examiner*—Robin Teskin
*Assistant Examiner*—Beth Burrous
*Attorney, Agent, or Firm*—Oblon, Spivak, McClelland, Maier & Neustadt

[57] ABSTRACT

DNA frangments containing an alkaline cellulase K gene, which comprise about 4.0, about 2.4 and about 1.9 kilo base pairs, respectively, each having a specific restruction map, recombinant plasmids containing any of these DNA fragments, and recombinant microorganisms harboring any of said plasmids.

The alkaline cellulase K gene is derived from a bacterial strain which belongs to the genus Bacillus and is alkalophilic, that is, capable of revealing an optimum growth in an alkaline pH region.

9 Claims, 10 Drawing Sheets

FIG.1-A
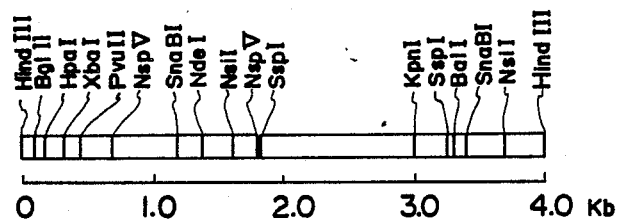
FIG.1-B
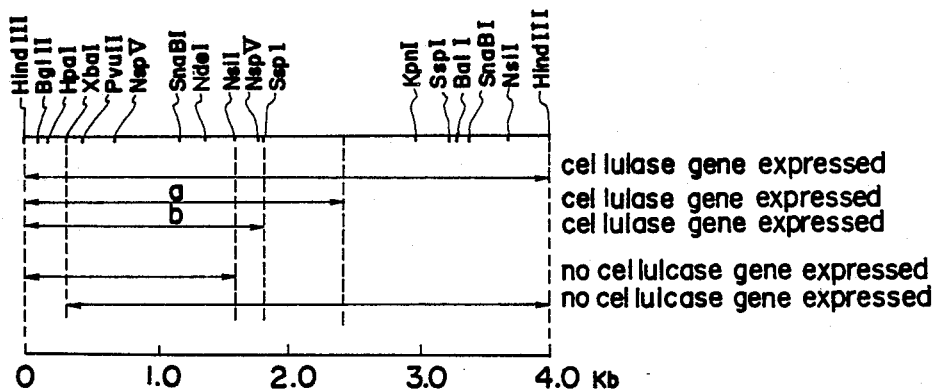

DNA FRAGMENTS CONTAINING ALKALINE CELLULASE GENE, RECOMBINANT PLASMIDS WITH SAID DNA FRAGMENTS INSERTED THEREIN, AND RECOMBINANT MICROORGANISMS

BACKGROUND OF THE INVENTION

1. Field of the Invention

This invention relates to DNA fragments containing an alkaline cellulase K gene derived from a bacterial strain which belongs to the genus Bacillus and is alkalophilic, i.e. capable of optimal growth in the alkaline pH region, to plasmids with said DNA fragments inserted therein, and further to transformant microorganisms transformed with such recombinant plasmids.

2. Description of the Prior Art

So far cellulase has been recognized as a group of complicated enzymes catalyzing those enzymatic reactions by which cellulose is degraded to glucose, cellobiose or cello-oligosaccharide. Cellulase is said to include those enzymes given the names of $C_1$ enzyme, $C_x$ enzyme, $\beta$-glucosidase, exo-$\beta$-glucanase, endo-$\beta$-glucanase, cellobiase and so forth according to the mechanisms of their action. For the past several decades studies on cellulase have searched for sources of cellulase supply among fungi, such as fungi of the genera Trichoderma, Aspergillus, Acremonium and Humicola, exclusively from the viewpoint of profitable utilization of biomass resources.

Recently, cellulase-containing detergent compositions for articles f clothing, for instance, are under development, where cellulase might find a novel industrial use. However, the great majority of cellulase species produced by microorganisms, inclusive of the above-mentioned fungi, are the so-called neutral or acid cellulase species which show optimal and stable enzymatic activity at neutral to acidic pH. The occurrence of the so-called alkaline cellulase which shows its highest activity and is stable at alkaline pH, hence can meet the requirements relative to detergent compositions for clothing items and is very rare. Thus, the methods so far known for the production of alkaline cellulase species having the possibility of their being used in detergent compositions for clothing items includes only the method of producing cellulase A which comprises cultivating an alkalophilic bacterial strain belonging to the genus Bacillus and recovering cellulase A from the culture medium (Japanese Patent Publication No. 50-28515), the method of producing alkaline cellulase 301-A which comprises cultivating a bacterial strain belonging to the genus Cellulomonas (Japanese Patent Application Laid-open No. 58-224686), the method of producing carboxymethyl cellulase which comprises cultivating the alkalophilic Bacillus strain No. 1139 [Fukumori, F., Kudo, T. and Horikoshi, K., J. Gen. Microbiol., 131, 3339 (1985)] and the method of producing alkaline cellulase which comprises using a strain of the genus Streptomyces (Japanese Patent Application Laid-open No. 61-19483). Meanwhile, very recently, it was found that Bacillus sp. KSM-635 (FERM BP-1485), a kind of alkalophilic bacteria, can produce alkaline cellulase K, which is suited for use in detergent compositions for clothing items, in significant quantities and, furthermore, its productivity was improved as a result of investigations on the method of cultivation. Thus the technology of industrial fermentative production of alkaline cellulase is making progress. On the other hand, even with this technology, the pH of the medium must be maintained on the alkaline side during cellulase fermentation and, in addition, further improvement in its potency is desired for realizing actual commercial production thereof.

Therefore, from the viewpoint of breeding by taking a genetic approach, it appears to be of very great significance to use gene manipulation techniques in an attempt to isolate the alkaline cellulase gene of an alkalophilic bacterial strain of the genus Bacillus, joining the resultant plasmid into a microorganism capable of growing under neutral conditions.

SUMMARY OF THE INVENTION

In an attempt to obtain a DNA fragment containing the alkaline cellulase K gene from the chromosomal DNA of an alkalophilic bacterial strain of the genus Bacillus, the present inventors, by making use of gene manipulation techniques, prepared a recombinant Escherichia strain capable of producing alkaline cellulase K and isolated from said bacterial strain an alkaline cellulase K gene-containing DNA fragment of about 4.0 kb. Furthermore, this DNA fragment of about 4.0 kb was analyzed for the locus containing the alkaline cellulase gene and it was found that said gene is contained in a DNA fragment of about 2.4 kb. Even when a still smaller DNA fragment of about 1.9 kb was used, the expression of said gene was noted. The inventors compared these DNA fragments with other cellulase genes isolated so far from bacterial strains of the genus Bacillus, namely the $\beta$-glucanase gene of Bacillus subtilis [Murphy, N., McConnell, D.J. and Cantwell, B.A., Nucleic Acids Res., 12, 5355 (1984)], the two alkaline cellulase genes of the alkalophilic Bacillus sp. strain N-4 [Sashihara, S., Kudo, T. and Horikoshi, K., J. Bacteriol., 158, 503 (1984)], the cellulase gene of Bacillus subtilis [Koide, Y., Nakamura, A., Uozumi, T. and Beppu, T., Agric. Biol. Chem., 50, 233 (1986), Nakamura, A., Uozumi, T., and Beppu, T., Eur. J. Biochem., 164, 317 (1987)] and the alkaline cellulase gene of the alkalophilic Bacillus sp. strain No. 1139 [Fukumori, F., Kudo, T., Narahashi, Y. and Horikoshi, K., J. Gen. Microbiol., 132, 2329 (1986)] and, as a result, found that said DNA fragments are novel DNA fragments having their own characteristic restriction maps. Based on the above findings, the present inventors have now accomplished the present invention.

The invention thus provides DNA fragments coding for alkaline cellulase K, more particularly DNA fragments respectively comprising about 4.0, about 2.4 and about 1.9 kilo base pairs and having the restriction maps shown in FIG. 1, FIG. 2 and FIG. 3, respectively, recombinant plasmids containing any of these DNA fragments, and recombinant microorganisms harboring any of said plasmids.

BRIEF DESCRIPTION OF THE DRAWINGS

FIG. 1-A shows the restriction map of the alkaline cellulase gene-containing, about 4.0 kb DNA fragment, and FIG. 1-B shows the ability or inability of various DNA fragments obtained from said 4.0 kb DNA fragment to cause expression of the alkaline cellulase gene;

DETAILED DESCRIPTION OF THE INVENTION AND PREFERRED EMBODIMENTS

Figure 2:
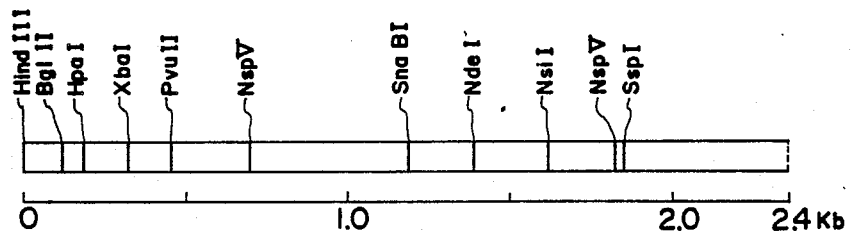
FIG. 2 shows the restriction map of the alkaline cellulase gene-containing, about 2.4 kb DNA fragment.

As the microorganism capable of serving as the alkaline cellulase gene donor in the practice of the invention, there may be mentioned, for example, Bacillus sp. KSM-635 (FERM BP-1485), a kind of alkalophilic bacteria of the genus Bacillus. This bacterial strain has been isolated by the present inventors from a soil sample collected in Haga-gun, Tochigi Prefecture, Japan as a strain capable of extracellularly producing alkaline cellulase K in significant amounts and has been deposited with the Fermentation Research Institute under the deposit number 1485. The taxonomic novelty of said strain has been detailedly described by the present inventors in Japanese Patent Application No. 61-257775 (filed on Oct. 28, 1986). The novelty of alkaline cellulase K which is produced in medium by said strain has also been described in detail by the present inventors in another patent application filed on the same date. This enzyme, namely alkaline cellulase K, has an optimum pH range on the alkaline side and primarily shows $C_x$ enzyme activity which is representative of the so-called CMCase acting on carboxymethyl cellulose (CMC). Furthermore, this alkaline cellulase K contains two main enzymes named CMCase I and CMCase II each having an optimum pH range in the alkaline region. Said two enzymes can be isolated by purification of the alkaline cellulase and their physicochemical properties have been made clear.

The chromosomal DNA can be obtained from the donor bacterial strain by the method of Marmur [Marmur, J., Mol. Biol., 3, 208 (1961)] or the method of Saito and Miura [Saito, H. and Miura, K. I., Biochim. Biophys. Acta, 72, 619 (1963)] or by some other similar method. Restriction enzyme cleavage of the chormosomal DNA thus obtained gives a DNA fragment containing the alkaline cellulase gene. For this purpose, any restriction enzyme may be used provided that it does not cleave the region of said gene. The use of HindIII is most preferred, which gives an about 4.0 kilo base DNA fragment containing said gene without cleaving said gene. Furthermore, alkaline cellulase gene-containing DNA fragments of about 2.4 kb and about 1.9 kb can be obtained by cleaving the above DNA fragment of about 4.0 kb with an appropriate restriction enzyme or the nuclease Bal 31, subcloning each DNA fragment obtained in a vector plasmid, and examining the recombinant microorganism obtained for cellulase production and thereby locating the site where the alkaline cellulase gene resides. Thus, the DNA fragment indicated by "a" in FIG. 1-B which has a length of about 2.4 kb can cause alkaline cellulase gene expression as well. The DNA fragment of about 1.9 kb indicated by "b" in FIG. 1-B also has been confirmed to cause expression of said gene although the expression efficiency may be decreased to some extent in certain cases. The cause of the decreased expression efficiency in such cases has not been explained as yet, although deletion of part of the alkaline cellulase gene, for instance part of the promoter region is suspected.

As the host-vector system for realizing gene recombination, any one can be used provided that the host strain can grow in the neutral pH range, that the alkaline cellulase K gene can be expressed, and that the vector is replicable in the host while stably retaining the insert gene in question. Thus, for example, the EK system in which Escherichia coli K-12 or a strain derived therefrom serves as the host and the BM system in which Bacillus subtilis Marburg or a strain derived therefrom may be mentioned. The use of the EK system which has been genetically studied most closely and for which a plenty of vectors are available gives good results. As examples of the host, there may be mentioned the strains HB101, C600 and JM109 for the EK system and the strains BD170 and MI112 for the BM system. As regards the vector, in addition to the above description, the use of a plasmid vector capable of being cleaved at one single site with that restriction enzyme which is used for cleaving the chromosomal DNA is convenient for ligation with the chromosomal DNA fragment. More specifically, for the case where the chromosomal DNA is cleaved with HindIII, there may be mentioned such vectors as pBR322, pUC12 and pUC18 for the EK system and such vectors as pC194 and pBD8 for the BM system. Other vectors having no cleavage site available for the restriction enzyme used for cleaving the chromosomal DNA can also be used if synthetic linkers are used or the homopolymer ligation method [Nelson, T. and Brutlag, D., Methods in Enzymology, 68, 41, Academic Press (1980)] or the like is employed on the occasion of ligation.

Ligation of the above chromosomal DNA fragment with the restriction enzyme-cleaved vector DNA gives a recombinant plasmid. The ligation is carried out, for example by the method using DNA ligase or by the homopolymer ligation method.

The method of transforming the host microbial strain with the recombinant plasmid is not critical. Thus, for example, the calcium chloride method [Mandel, M. and Higa, A., J. Mol. Biol., 53, 159 (1970)] and the rubidium chloride method [Bolivar, F. and Backman, K., Methods in Enzymology, 68, 253, Academic Press (1979)] may be used for the EK system host strains, and the competent cell method [Contente, S. and Dubnau, D., Mol. Gen. Genet., 167, 251 (1979)] and the protoplast method [Chang, S. and Cohen, S.N., Mol. Gen. Genet., 168, 111 (1979)] for the BM system host strains. For transformant selection, a character encoded on the vector plasmid and resistant to inactivation due to insertion of the foreign chromosomal DNA, for example an antibiotic resistance, is first used as an index in primarily selecting transformants carrying the vector plasmid. More specifically, when, for example, pBR322 of the EK system is employed as the vector plasmid and the HindIII fragment of the chromosomal DNA is inserted into said plasmid at the HindIII site thereof, the tetracycline resistance gene is inactivated by the insertion of the foreign DNA into pBR322 at the HindIII cleavage site thereof but the ampicillin resistance can be used as an index to primary selection since the gene for ampicillin resistance has no HindIII cleavage site therein. The transformants thus selected are then transferred to an appropriate agar medium containing 2% of CMC by the replica palting method, and cultured. After appearance of colonies, successfully transformed colonies can be selected by the Congo red method [Teather, R. M. and Wood, P. J., Appl. Environ. Microbiol., 43, 777 (1982)] since such colonies decompose CMC occurring around them.

The recombinant plasmid carried by a transformant obtained in the above manner can be recovered by a conventional plasmid preparation method [Maniatis, T. et al, Molecular Cloning, Cold Spring Harbor Laboratory (1982); Yasutaka Takagi (ed.), Idenshi Sosa Manual (Gene Manipulation Manual), Kodansha (1982); etc.]. Identification of the thus-obtained recombinant plasmid as the plasmid resulting from joining of the vector plasmid with the alkaline cellulase gene-containing DNA fragment can be performed by analyzing the pattern of cleavage of said recombinant plasmid with various enzymes by electrophoresis, for invention is contained in a 4.0 kb DNA fragment the both ends of which are HindIII sites, as shown in FIG. 1. This 4.0 kb DNA fragment is characterized by the occurrence therein of one BglII cleavage site, one HpaI cleavage site, one XbaI cleavage site, one PvuII cleavage site, one NdeI cleavage site, one BalI cleavage site and one KpnI cleavage site, two NsiI cleavage sites, two NspV cleavage sites, two SnaBI cleavage sites and two SspI cleavage sites, and the absence of any BamHI, ClaI, EcoRI, EcoRV, NruI, PstI, PvuI, SalI, ScaI or SphI site, as confirmed by agarose gel electrophoresis. The two DNA fragments of about 2.4 kb and about 1.9 kb have the restriction enzyme cleavage sites shown in FIG. 2 and FIG. 3, respectively, as revealed by agarose gel electrophoresis. No BamHI, ClaI, EcoRI, EcoRV, NruI, PstI, PvuI, SalI, ScaI or SphI sites were found.

Known as the cellulase genes so far isolated from bacteria of the genus Bacillus are the β-glucanase gene of *Bacillus subtilis* [Murphy, N., McConnell, D. J. and Cantwell, B. A., Nucleic Acids Res., 12, 5355 (1984)], the two alkaline cellulase genes of alkalophilic Bacillus sp. N-4 [Sashihara, S., Kudo, T. and Horikoshi, K., J. Bacteriol., 158, 503 (1984)], the cellulase gene of *Bacillus subtilis* [Koide, Y., Nakamura, A., Uozumi, T. and Beppu, T., Agric. Biol. Chem., 50, 233 (1986), Nakamura, A., Uozumi, T. and Beppu, T., *Eur. J. Biochem.*, 164, 317 (1987)] and the alkaline cellulase gene of alkalophilic Bacillus sp. strain No. 1139 [Fukumori, F., Kudo, T., Narahashi, Y. and Horikoshi, K., J. Gen. Microbiol., 132, 2329 (1986)]. Comparison of the restriction maps of the alkaline cellulase gene-containing DNA fragments according to the invention with those of DNA fragments containing the above-mentioned genes has revealed that the DNA fragments according to the invention are clearly novel ones each having its own distinct restriction map.

Figure 3:
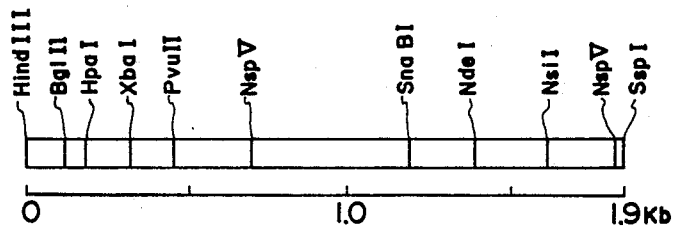
FIG. 3 shows the restriction map of the alkaline cellulase gene-containing, about 1.9 kb DNA fragment.
Figure 4:
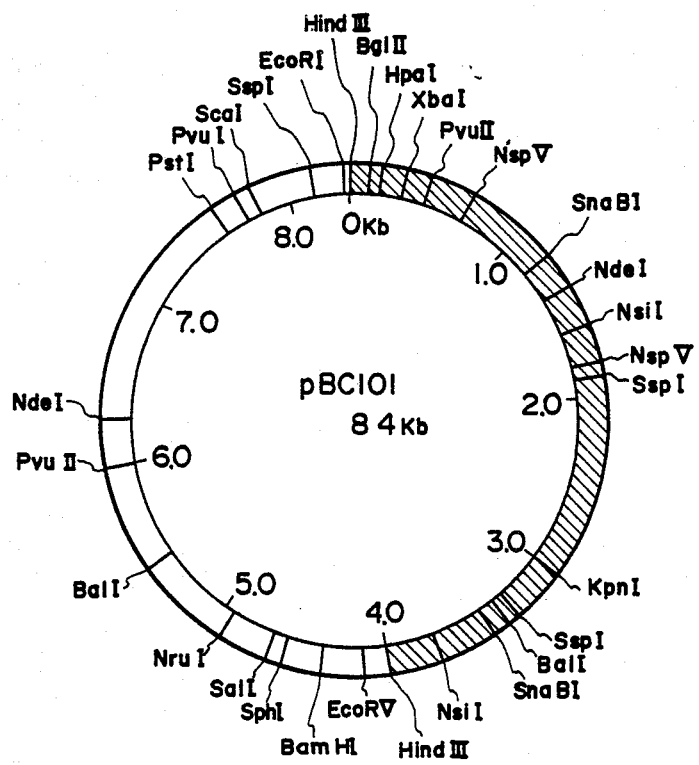
FIG. 4, FIG. 5, FIG. 6, FIG. 7, FIG. 8 and FIG. 9 respectively show the restriction maps of the recombinant plasmids pBC101, pBC102, pBCll, pBC112, pBC113 and pBC114, where the white, unreticulated segment indicates the vector pBR322-derived DNA fragment and the reticulated segment indicates the Bacillus sp. KSM-635-derived DNA fragment.
Figure 5:
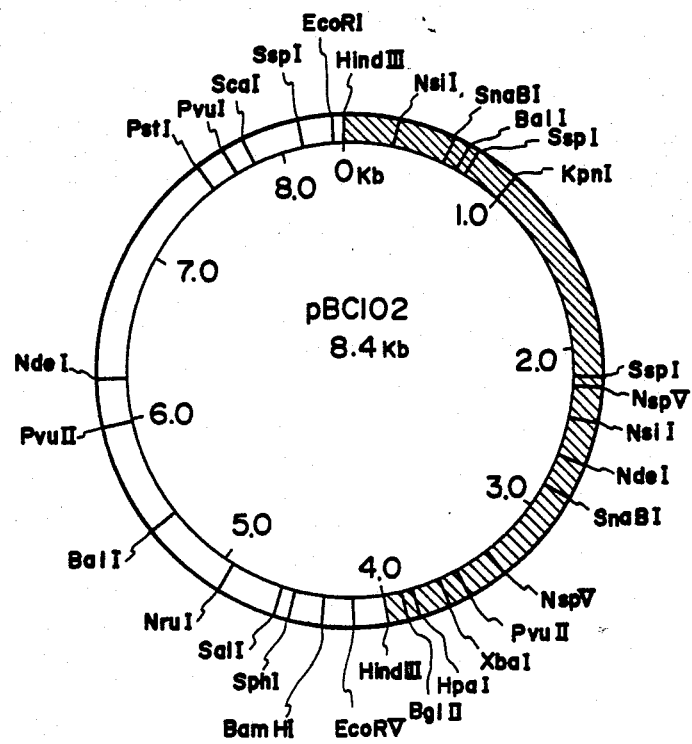
Figure 6:
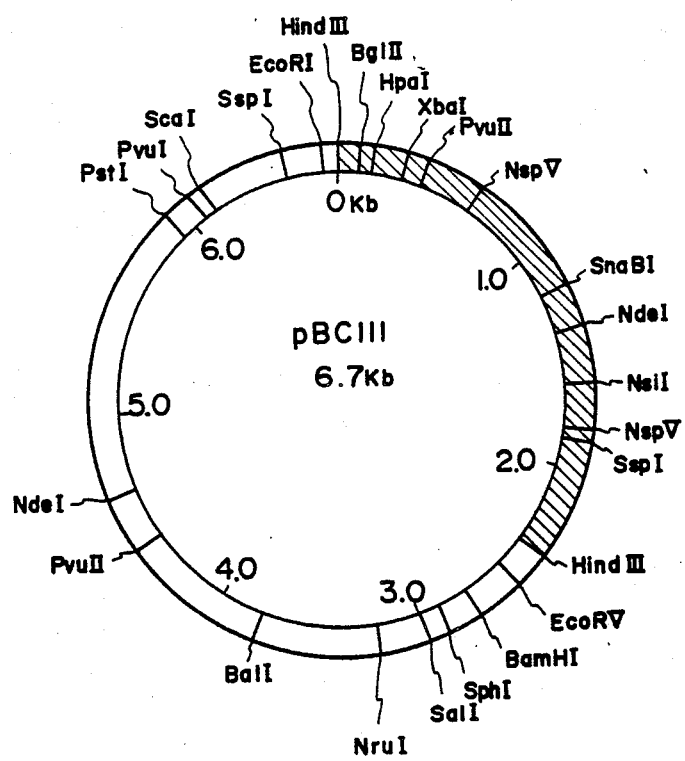
Figure 7:
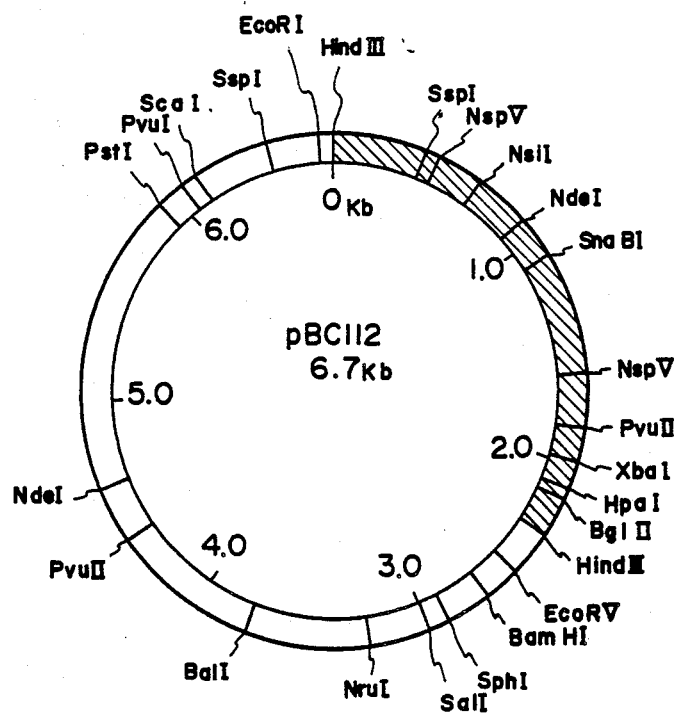
Figure 8:
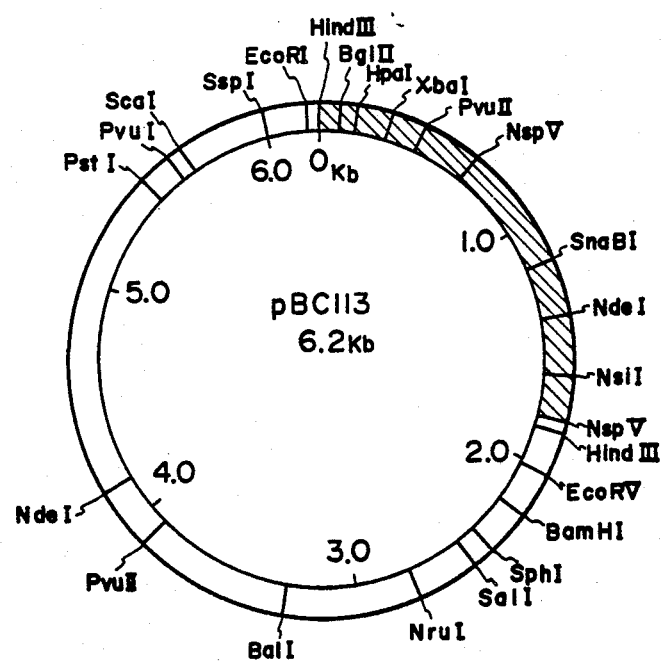
Figure 9:
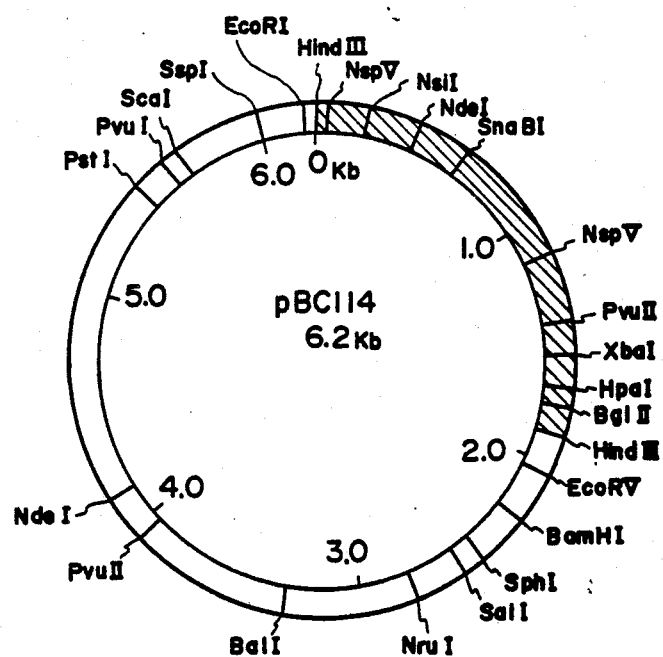

As suitable examples of the recombinant plasmid containing the alkaline cellulase gene according to the invention, there may be mentioned the recombinant plasmids pBC101 (FIG. 4), pBC102 (FIG. 5), pBC111 (FIG. 6), pBC112 (FIG. 7), pBC113 (FIG. 8) and pBC114 (FIG. 9), among others. All the recombinant plasmids mentioned above are products of insertion of a chromosomal DNA fragment containing the KSM-635-derived alkaline cellulase gene into the vector plasmid pBR322 at the HindIII cleavage site thereof. In the case of pBC101 and pBC102, the insert DNA fragment is that fragment of about 4.0 kb which is shown in FIG. 1. In the case of pBC111 and pBC112, the insert is that fragment of about 2.4 kb which is shown in FIG. 2 and, in the case of pBC113 and pBC114, it is that fragment of about 1.9 kb which is shown in FIG. 3. In joining the about 2.4 kb and about 1.9 kb DNA fragments having no HindIII cleavage site at one end thereof to the vector plasmid, said fragments were provided with a synthetic HindIII linker. In the pairs pBC101 and pBC102, pBC111 and pBC112, and pBC113 and pBC114, the directions of the insert DNA fragment relative to the vector plasmid pBR322 are reverse to each other in each pair.

The use of any of these recombinant plasmids can lead to expression of said gene in a host bacterial strain. This indicates that the expression of said gene does not depend on any promoter region encoded on the vector plasmid, for example the promoter region of the tetracycline gene, but depends on an intrinsic promoter region of said gene. As suitable examples of the recombinant microorganism transformed with said recombinant plasmid, there may be mentioned the *Escherichia coli* strains HB101(pBC101), HB101(pBC102), HB101(pBC111), HB101(pBC112), HB101(pBC113) and HB101(pBC114), among others. These are strains derived from the strain HB101 by introduction of the recombinant plasmids pBC101, pBC102, pBC111, pBC112, pBC113 and pBC114, respectively. When cultivated in a medium ordinarily used in cultivating bacteria of the genus Escherichia, for example LB medium, they produce alkaline cellulase intracellularly. The optimum reaction curve for the enzyme thus produced shows a maximum at pH 8-10 and is in good agreement with that for alkaline cellulase K produced by the gene donor strain, namely Bacillus sp. KSM-635 (FERM BP-1485). In addition, the immunological identity of both the enzymes produced by the transformants on one hand and the gene donor strain on the other was confirmed by an immunodiffusion test. The strain *Escherichia coli* HB101(pBC101) has been deposited with the Fermentation Research Institute under the deposit number FERM-8967.

The alkaline cellulase gene-containing DNA fragment can be isolated from the recombinant plasmid by cleaving the recombinant plasmid with the restriction enzyme HindIII, separating the DNA fragment by agarose gel electrophoresis and extracting and purifying said fragment from the gel. For extraction and purification of the DNA fragment from the gel, the electroelution method [McDonnell, M. W., Simon, M. N. and Studier, F. W., J. Mol. Biol., 110, 119 (1977)] or the method using a low-melting-temperature agarose gel [Weislander, L., Anal. Biochem., 98, 305 (1979)], for instance, may be used. The DNA fragment obtained may be about 4.0 kb, about 2.4 kb or about 1.9 kb long depending on the kind of the recombinant plasmid used. In any case, however, the DNA fragment can be ligated easily with some other vector cleaved with the same enzyme HindIII since both ends of said DNA fragment are HindIII cleavage ends.

The following examples illustrate the invention in further detail.

In the examples, CMCase activity measurement was performed as follows: 0.1 ml of the enzyme solution to be assayed was added to a substrate solution composed of 0.2 ml of 2.5% CMC, 0.1 ml of 0.5 M glycine buffer (pH 9.0) and 0.1 ml of deionized water. After completion of the reaction at 40° C. reducing sugars produced were assayed by the 3,5-dinitrosalicylic acid (DNS) method [Sakuzo Fukui, "Kangento no Teiryoho (Assay Methods for Reducing Sugars)", Gakkai Shuppan Center, Sumuer, J. R. and Somers, G. F., Laboratory experiments in biological chemistry, Academic Press, p. 34, (1944)]. In expressing enzyme potencies, the quantity of enzyme required to produce, under the above-mentioned conditions, reducing sugars in an amount equivalent to 1 μmol of glucose per minute was defined as 1 unit (1 U). Protein assay was conducted using Bio-Rad protein assay kit and protein quantity calculation was made with bovine plasma albumin as a standard protein.

EXAMPLE 1

Bacillus sp. KSM-635 (FERM Bp-1485), one of alkaline cellulase-producing alkalophilic Bacillus strains, was inoculated into 5 ml of MYG medium [1.0% meat extract (Lab-Lemco Powder, Oxoid), 0.5% yeast extract (Difco), 1.0% NaCl, 0.1% $KH_2PO_4$, 1.0% $Na_2CO_3$ (separately sterilized)], and shake culture was performed at 30° C. for 2 days. The culture was inoculated into 500 ml of the same medium and shake culture was conducted at 30° C. further for 30 hours. Then, cells were harvested by centrifugation, and 250 μg of purified chromosomal DNA was obtained by the method of Saito and Miura [Saito, H. and Miura, K. I., Biochim. Biophys. Acta, 72, 619 (1963)].

EXAMPLE 2

10 μg of the chromosomal DNA obtained in Example 1 and 1 μg of the vector plasmid pBR322 (Boehringer Mannheim GmbH) were dissolved in a restriction enzyme reaction medium [10 mM Tris-HCl buffer (pH 7.5), 10 mM $MgCl_2$, 50 mM NaCl, 1 mM dithiothreitol, 20 units of the restriction enzyme HindIII (Boehringer Mannheim) was added to the solution, and the reaction was conducted at 37° C. for 2 hours. Thereafter, the restriction enzyme was removed by treatment with phenol, which was followed by precipitation with ethanol. The thus-obtained DNA precipitate was dissolved in 50 μl of ligase reaction medium [20 mM Tris-HCl buffer (PH 7.5), 10 mM $Mgcl_2$, 10 mM dithiothreitol, 1 mM ATP]. 2 units of $T_4$ DNA ligase (Boehringer Mannheim GmbH) was added to the solution, and the reaction was carried out at 16° C. for 12 hours, whereby the chromosomal DNA fragment and the vector plasmid were joined together to give a recombinant plasmid.

EXAMPLE 3

The recombinant plasmid constructed in Example 2 was used to transform a strain of *Escherichia coli* by the calcium chloride method [Mandel, M. and Higa, A., J. Mol. Biol., 53, 159 (1970)]. The host strain used was *Escherichia coli* HB101 (leu, pro, thi, lacY, ara14, gaik2, xy15, mtll, strA, recA, supE44, hsdr, hsdM, endI). The cell suspension obtained after transformation treatment was spread onto LB agar medium [1.0% tryptone (Difco), 0.5% yeast extract (Difco), 1.0% NaCl, 1.5% Bacto-agar (Difco)]containing 50 μg/ml of ampicillin (sodium salt, Sigma) and incubated at 37° C. for 24 hours. About 10,000 transformant colonies that had appeared were transferred to LB agar medium containing 50 μg/ml of ampicillin and 2% of CMC by the replica plating method and further incubated at 37° C. for 48 hours. Thereafter, strains that had decomposed CMC around the colonies thereof were selected by the Congo red method [Teather, R. M. and Wood, R. J., Appl. Environ. Microbiol., 43, 777 (1982)]. Thus were isolated 8 strains as the desired transformants.

EXAMPLE 4

The eight transformant strains obtained in Example 3 were each inoculated into 10 ml of LB medium [1.0% tryptone (Difco), 0.5% yeast extract (Difco), 1.0% NaCl] containing ampicillin (50 μg/ml). After overnight stationary culture at 37° C., each culture was transferred to 1 liter of M9CA medium [0.6% $Na_2PO_4$, 0.3% $KH_2PO_4$, 0.05% NaCl, 0.1% $NH_4Cl$, 0.2% Casamino acids (Difco), 2 mM $MgSO_4$ (separately sterilized), 0.1 mM $CaCl_2$ (separately sterilized), 0.2% glucose (separately sterilized, 50 μg/ml ampicillin (sterilized by filtration)], and shake culture was conducted at 37° C. for 4–5 hours. Then lb 170 mg of chloraphenicol was added, and shake culture was further carried out at 37° C. for 15 hours. Cells were harvested from each culture by centrifugation, and the recombinant plasmid was prepared by the method of Maniatis el al [Maniatis, T. et al, Molecular Cloning, Cold Spring Harvor Laboratory (1982)]which is a combination of the alkaline lysis method [Birnboim, H. C. and Doly, J., Nucleic Acids Res., 7, 1513 (1979)]and the cesium chloride-ethidium bromide density gradient centrifugation method ]Radloff, R., Bauer, W. and Vinograd, J., Proc. Natl. Acad. Sci. USA, 57, 1514 (1967)]. A 1 μg portion of each of the thus-obtained eight recombinant plasmids was dissolved in a restriction enzyme reaction medium [10 mM Tris-HCl buffer (pH 7.5), 10 mM $MgCl_2$, 50 mM NaCl, 1 mM dithiothreitol], 5 units of the restriction enzyme HindIII (Boehringer Mannheim GmbH) was added to the solution, the reaction was conducted at 37° C. for 2 hours and, then, cleavage pattern analysis was carried out by the agarose gel electrophoresis method. The eight recombinant plasmids were thus found to contain a common 4.0 kb DNA fragment in addition to pBR322 (4.4 kb). For two plasmids smallest in size among them, restriction maps were constructed by the conventional method [e.g. Maniatis, T. et al, Molecular Cloning, Cold Spring Harbor Laboratory (1982)]. Both the recombinant plasmids were thus found to consist of the 4.0 kb DNA fragment shown in FIG. 1 and the vector pBR322 as joined together, with the directionality of the insert DNA fragment relative to the vector in one of them being reverse to that in the other. This 4.0 kb DNA fragment was found to have cleavage sites with respect to BglII, XbaI, KpnI, BalI, HpaI, PvuII, NspV, NdeI, SnaBI, SspI and NsiI, as shown in FIG. 1, but have no cleavage sites with respect to BamHI, ClaI, EcoRI, EcoRV, NruI, PstI, PvuI, SalI, ScaI and SphI. The two recombinant plasmids obtained were named pBC101 (FIG. 4) and pBC102 (FIG. 5), respectively, and the *Escherichia coli* HB101-derived transformants respectively carrying pBC101 and pBC102 were named HB101(pBC101) and HB101(pBC102), respectively.

Example 5

1 μg of pBC101 was dissolved in 50 μl of a 10 mM Tris-HCl buffer solution (pH 7.5) containing 10 mM $MgCl_2$ and 1 mM dithiothreitol, 2 units of the restriction enzyme KpnI was added to the solution, and the reaction was conducted at 37° C. for 2 hours to obtain linear pBC101. Thereafter, the KpnI was removed by treatment with phenol, followed by precipitation with ethanol. The thus obtained precipitate was dissolved in a 50 mM Tris-HCl buffer solution containing 10mM MgSO$_4$ and 0.1 mM dithiothreitol. 1.25 units of nuclease Bal31 was added to the solution, and the reaction was carried out at 22° C. for 15 minutes. The reaction was terminated by treatment with phenol, followed by precipitation with ethanol. The above obtained precipitate was dissolved in 50 μl of a 10mM Tris-HCl buffer solution containing 10 mM MgCl$_2$, 1mM dithiothreitol and 50 mM NaCl. One unit of the restriction enzyme HindIII was added to the solution, and the reaction was carried out at 37° C. for 2 hours. Thereafter, about 2.4 Kb DNA fragment was isolated by an agarose gel electrophoresis.

Figure 10:
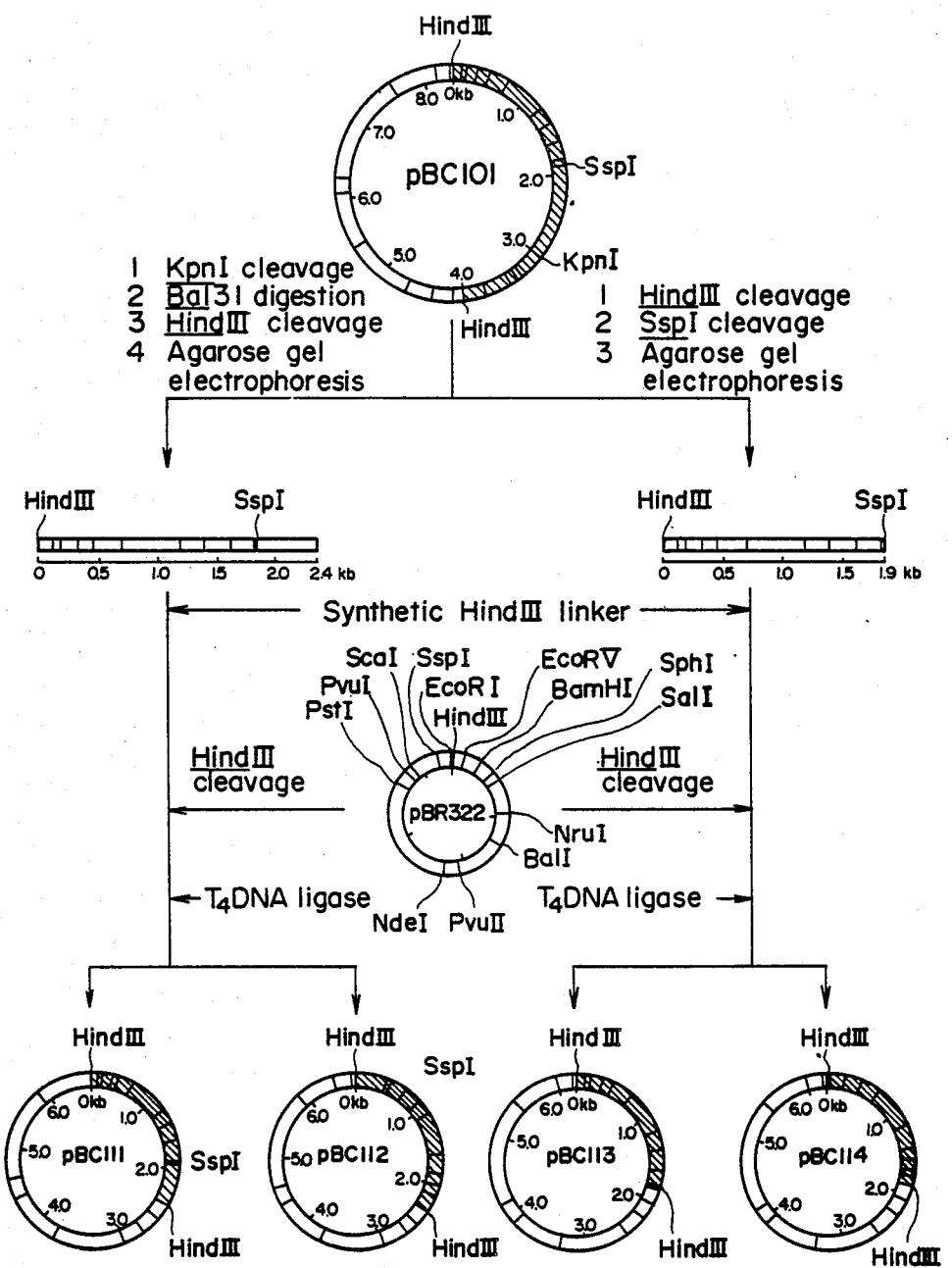
FIG. 10 shows a process of subcloning.

The DNA fragment of about 1.9 Kb was isolated in accordance with the following manner. Namely, 1 μg of pBC101 was dissolved in a 50 mM Tris-HCl buffer solution (pH 7.5) containing 10 mM MgCl$_2$, 1mM dithiothreitol and 100 mM NaCl. 2 units of the restriction enzyme HindIII and 2 units of SspI were added to the above obtained solution, followed by reaction at 37° C. for 2 hours. Thereafter, the DNA fragment of about 1.9 was isolated by an agarose gel electrophoresis. After joining of synthetic HindIII linkers (Pharmacia), these DNA fragments were again joined to the vector plasmid pBR322 using T$_4$ DNA ligase and the ligation products were used to transform Escherichia coli HB101. The transformants obtained were transferred to LB agar medium containing CMC by the replica plating method. After 1-2 day cultivation at 37° C., the transformants were examined for alkaline cellulase productivity by the Congo red method. That each DNA fragment in question had been inserted in the vector plasmid pBR322 was confirmed following extraction of the plasmid from the corresponding transformant by the same method as used in Example 4. Recombinant microorganisms carrying the recombinant plasmid resulting from joining of the DNA fragment shown in FIG. 1-B by a symbol "a" (about 2.4 kb) or the DNA fragment shown in FIG. 1-B by a symbol "b" (about 1.9 kb), each included in the DNA fragment of about 4.0 kb, to the vector plasmid showed cellulase productivity irrespective of the direction of insertion of the insert DNA fragment. With the DNA fragment of about 1.9 kb, however, the clear zone as revealed by the Congo red method was narrow and a slight decrease in alkaline cellulase gene expression efficiency was thus suggested. On the other hand, when the DNA fragment of about 4.0 kb was deprived of the DNA fragment from the HindIII site to the XbaI site (about 0.3 kb) or the DNA fragment from the NsiI site to the HindIII site (about 2.3 kb), expression of the gene in question was not observed. The above findings led to the conclusion that the alkaline cellulase gene is contained in the above-mentioned, about 2.4 kb or about 1.9 kb DNA fragment and that the expression of said gene depends on its own promoter region and, on the other hand, it was suggested that the XbaI and NsiI cleavage sites be present within said gene. As regards the DNA fragment of about 1.9 kb, the decreased level of gene expression suggested partial deletion of the gene, for example partial deletion in the promoter region. The recombinant plasmids resulting from insertion of the DNA fragment of about 2.4 kb, with a synthetic HindIII linker joined thereto, into the vector plasmid pBR322 at the HindIII cleavage site thereof were named pBC111 and pBC112, while the recombinant plasmids obtained by insertion of the DNA fragment of about 1.9 kb, with a synthetic HindIII linker added thereto, into the vector plasmid pBR322 at the HindIII cleavage site thereof were named pBC113 and pBC114. The above-mentioned process of subcloning is illustrated in FIG. 10. The strains obtained by transformation of Escherichia coli HB101 with the respective recombinant plasmids were named HB101(pBC111), HB101(pBC112), HB101(pBC113) and HB101(pBC114).

EXAMPLE 6

After overnight stationary culture of the strain Escherichia coli HB101(pBC101), HB101(pB102), HB101(pBC111), HB101(pBC112), HB101(pBC113) or HB101(pBC114) in 10 ml of LB medium, 1 ml of the culture was inoculated into 100 ml of LB medium (containing 50 μg/ml of ampicillin), and shake culture was carried out at 37° C. for 24 hours. Thereafter, the culture broth was centrifuged, and the cells obtained as a sediment were suspended in 10 ml of phosphate buffer (pH 7.0) and sonicated. Centrifugation was again conducted to remove the insoluble matter as a sediment. The supernatant thus obtained was used as a cell-free extract. In a control run, the strain HB101(pBR322) was used and a cell-free extract was prepared in the same manner. The cell-free extracts prepared in this way were assayed for CMCase activity. As shown in Table 1, the cell-free extracts from the strains HB101(pB101), HB101(pBC102), HB101(pBC111), HB101(pBC112), HB101(pBC113) and HB101(pBC114) showed CMCase activity (in glycine buffer, pH 9.0).

TABLE 1

| Strain | Growth rate (OD$_{600\ nm}$) | CMCase activity (mU/mg protein) |
|---|---|---|
| HB101(pBC101) | 4.8 | 2.2 |
| HB101(pBC102) | 5.3 | 2.6 |
| HB101(pBC111) | 5.1 | 2.3 |
| HB101(pBC112) | 5.2 | 2.4 |
| HB101(pBC113) | 5.3 | 1.6 |
| HB101(pBC114) | 5.0 | 1.3 |
| HB101(pBR322) | 5.2 | 0 |

Figure 11:
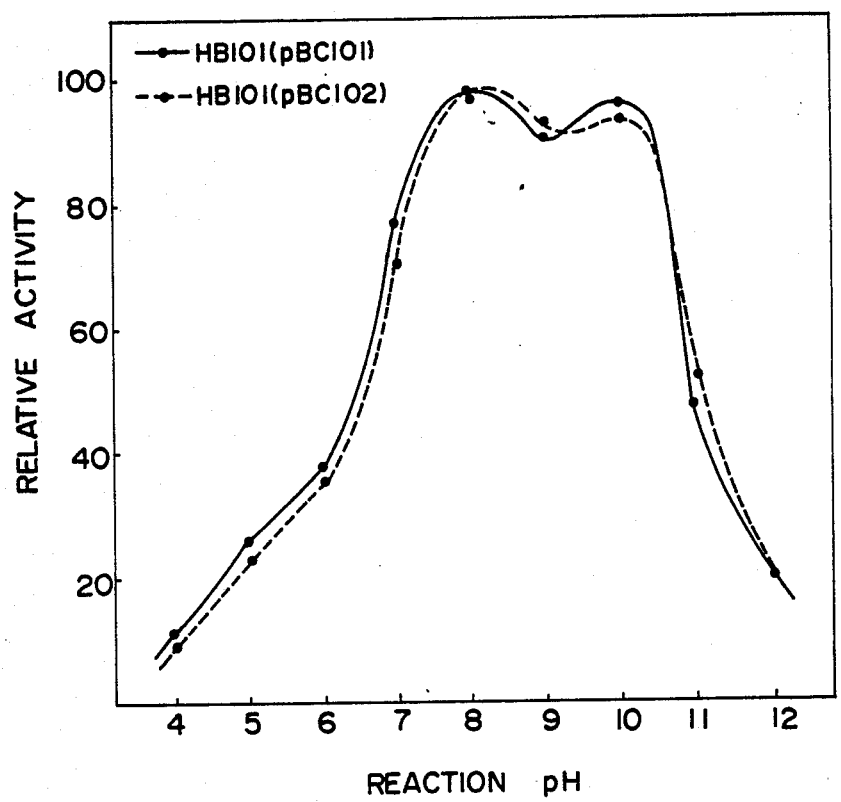
FIG. 11 is a graph showing the pH range within which the alkaline cellulase produced by the strains HB101(pBC101) and HB101(pBC102) can exhibit its activity, with an optimum pH for its activity.

Furthermore, the intracellular CMCase produced was examined for the pH range in which it was active and for the optimum pH for its activity (FIG. 11), and it was found that this enzyme can exhibit its activity within the broad pH range of 4–12, with an optimum pH at 8–10. These properties were in good agreement with those of alkaline cellulase K produced by the gene donor Bacillus sp. KSM-635 (FERM Bp,1485).

Figure 12:
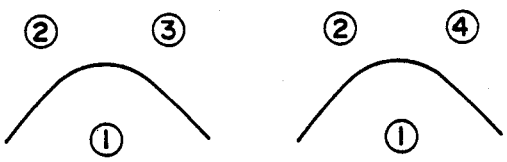
FIG. 12 shows the results of double immunodiffusion performed with the alkaline cellulase produced by HB101(pBC101) and CMCase I purified from Bacillus sp. KSM-635, where ① indicates an antiserum against purified CMCase II, ② indicates purified CMCase, and ③ and ④ indicate the alkaline cellulase species produced by the strains HB101(pBC101) and HB101(pBC102), respectively.

In double immunodiffusion [e.g. Shigeru Muramatsu et al, "Jikken Seibutsugaku Koza (Lectures in Experimental Biology), vol. 14, Men-eki Seibutsugaku (Immunobiology)", Ouchterlony, O., Acta Pathol. Microbial. Scand., 25, 186, (1948)], the alkaline cellulase produced by the strains HB101(pBC101) and HB101(pBC102) gave a precipitation line as a result of reaction with an antiserum against CMCase II purified from a culture of the strain KSM-635, and this precipitation line completely fused with that formed by CMCase II. Thus was indicated the immunological identity of both the enzymes (FIG. 12).

REFERENCE EXAMPLE (i) One gram of a soil sample collected in Ichikaimachi, Haga-gun, Tochigi Prefecture, Japan was suspended in 10 ml of sterilized physiological saline and heat-treated at 80° C. for 30 minutes. The heat-treated liquid was appropriately diluted and the dilution was spread onto a master plate [1% meat extract (Oxoid), 1% Bactopeptone (Difco), 1% NaCl, 0.1% $KH_2PO_4$, 0.5% $Na_2CO_3$ (separately sterilized), 1.5% Bactoagar]. After 3-day cultivation at 30° C., the colonies that had formed were transferred, by the replica plating method, to a sterilized agar medium prepared by adding 2% CMC to the same medium as the master plate. After cultivation at 30° C. for 3–4 days for colony formation, a Congo red dye solution was poured onto the plate to thereby detect colonies around which the agar remained unstained on a reddened background. The corresponding colonies were picked out from the master plate and screened for high-potency CMCase producers.

Using the above technique, there was obtained Bacillus sp. KSM-635 (FERM BP 1485).

(ii) Bacillus sp. KSM-635 (FERM BP 1485) was cultured in a liquid medium containing 1.5% meat extract, 0.5% yeast extract, 1% CMC, 0.1% $KH_2PO_4$ and 0.75% $Na_2CO_3$ (separately sterilized) under aerobic conditions at 34° C. for 2 days. To 1 liter of the culture supernatant was added 3 liters of cold ethanol ($-10°$ C.) portionwise. The protein precipitate thus obtained was dissolved in a minimum amount of sterilized deionized water, and the solution was neutralized with diluted acetic acid and dialyzed against flowing water for 15 hours. Lyophilization gave 9.6 g of powdery alkaline cellulase K. The physicochemical properties of this product were as described later herein.

(iii) The alkaline cellulase K produced in the medium by the strain KSM-635 was purified in the following manner. Thus, cells were removed from the culture broth by centrifugation, and the supernatant was subjected to treatment with streptomycin and fractionation with ammonium sulfate. The precipitate fraction obtained at 30–75% saturation was subjected in sequence to preparatory high-performance liquid chromatography (SW 3000 G column, Toyo Soda), DEAE-Toyopearl (Toyo Soda) chromatography, hydroxyapatite (Seikagaku Kogyo) chromatography and, again, DEAE-Tyopearl chromatography. Elution on a linear NaCl concentration gradient (0.25M–0.35M) in the second DEAE-Toyopearl chromatography fractioned the enzyme into two CMCase species (CMCase I and CMCase II). Both the enzyme species were electrophoresed by the method of Davis [Davis, D. J., Ann. N.Y. Acad. Sci., 121, 404 (1964)]. Staining with Coomassie Briliant Blue gave a single band.

An antiserum against CMCase II was prepared by injecting a rabbit with the above purified CMCase II (1 mg per injection) in the conventional manner [e.g. Immunological Society of Japan (ed.), Men-ekigaku Jikkenho (Experiments in Immunology), parts A and B, Ouchterlony, O., Acta Pathol. Microbiol. Scand., 25, 186 (1948)].

[Physicochemical properties of alkaline cellulase K]

The physicochemical properties of alkaline cellulase K are as follows:

(1) Activity:
It has $C_x$ enzyme activity, namely acts on CMC and, in addition, has weak $C_1$ enzyme activity and $\beta$-glucosidase activity.

(2) Substrate specificity:
It acts on CMC, crystalline cellulose, Avicel, cellobiose and p-nitrophenyl-cellobioside.

(3) pH range within which it is active, and optimum pH:
It is active at pH 4–12, with an optimum pH at 9–10.

(4) pH range within which it is stable:
When allowed to stand at 40° C. for 10 minutes and 30 minutes, it is stable at pH 4.5–10.5 and 6.8–10, respectively.

(5) Temperature range within which it is active, and optimum temperature for its action:
It is active within the broad range of 10°–65° C., with an optimum temperature at about 40° C.

(6) Influence of chelating agents:
Its activity is not inhibited by EDTA, EGTA, NTA, STPP or zeolite.

(7) Influence of surfactants:
Its activity is little inhibited by linear alkylbenzenesulfonic acid sodium salt (LAS), alkylsulfate ester sodium salt (ES), polyoxyethylenealkylsulfate ester sodium salt (ES), $\alpha$-olefinsulfonic acid sodium salt (AOS), $\alpha$-sulfonated fatty acid ester sodium salt ($\alpha$-SFE), sodium alkylsulfonate (SAS), polyoxyethylene secondary alkyl ether, fatty acid salt (sodium salt), dimethyldialkylammonium chloride, and the like surfactants.

(8) Influence of protease:
It has strong resistance to protease.

(9) Molecular weight (gel chormatography method):
It shows a maximum peak at 180,000±10,000.

What is claimed is:

1. A DNA fragment coding for alkaline cellulase K which comprises about 4.0 kilo base pairs and has the restriction map shown in FIG. 1A. wherein said DNA fragment is isolated from Bacillus sp. Ksm-635.

2. A DNA fragment of claim 1, which comprises about 2.4 kilo base pairs and has the restriction map shown in FIG. 2, wherein said DNA fragment is isolated from Bacillus sp. Ksm-635.

3. A DNA fragment of claim 1, which comprises about 1.9 kilo base paris and has the restriction map shown in FIG. 3, wherein said DNA fragment is isolated from Bacillus sp. Ksm-635.

4. A recombinant plasmid which contains a DNA fragment coding for alkaline cellulase K wherein said DNA fragment comprises about 4.0 kilo base paris and has the restriction map shown in FIG. 1, wherein said DNA fragment is isolated from Bacillus sp. Ksm-635.

5. A recombinant plasmid of claim 4, wherein said DNA fragment comprises about 2.4 kilo base pairs and has the restriction map shown in FIG. 2, wherein said DNA fragment is isolated from Bacillus sp. Ksm-635.

6. A recombinant plasmid of claim 4, wherein said DNA fragment comprises about 1.9 kilo base pairs has the restriction map shown in FIG. 3, wherein said DNA fragment is isolated from Bacillus sp. Ksm-635.

7. A transformed microorganism carrying a recombinant plasmid which contains a DNA fragment coding for alkaline cellulase K wherein said DNA fragment comprises about 4.0 kilo base pair and has the restriction map shown in FIG. 1, wherein said DNA fragment is isolated from Bacillus sp. Ksm-635.

8. A transformed microorganism of claim 7, wherein said DNA fragment comprises about 2.4 kilo base pairs and has the restriction map shown in FIG. 2, wherein said DMA fragment is isolated from Bacillus sp. Ksm-635.

9. A transformed microorganism of claim 7, wherein said DNA fragment comprises about 1.9 kilo base pairs and has the restriction map shown in FIG. 3, wherein said DNA fragment is isolated from Bacillus sp. Ksm-635.

* * * * *

UNITED STATES PATENT AND TRADEMARK OFFICE
CERTIFICATE OF CORRECTION

PATENT NO. : 4,904,599

DATED : February 27, 1990

INVENTOR(S) : Ozaki et al.

It is certified that error appears in the above-identified patent and that said Letters Patent is hereby corrected as shown below:

In the Abstract, line 1, "frangments" should read

--fragments-- line 4, "restruction" should read "restriction"

Column 1, line 32, "articles f" should read --articles of--

Column 3, line 3, "pBC11" should read --pBC111--

Column 8, line 20, "separately sterilized," should read --separately sterilized),-- line 22, delete "1b", "chloraphenicol" should read --chloramphenicol-- line 32, change "]" to --[--

Column 10, line 15, "(pB102)" should read --(pBC102)-- line 30, "(pB101)" should read --(pBC101)--

Column 11, line 43, "Tyopearl" should read --Toyopearl-- line 50, "Briliant" should read --Brilliant--

UNITED STATES PATENT AND TRADEMARK OFFICE
CERTIFICATE OF CORRECTION

PATENT NO. : 4,904,599
DATED : FEBRUARY 27, 1990
INVENTOR(S) : Katsuya OZAKI et al It is certified that error appears in the above-identified patent and that said Letters Patent is hereby corrected as shown below:

Column 12, line 30: "IA." should read -- 1A, --;

line 31: "Ksm" should read --KSM--;

line 35: "Ksm" should read --KSM--;

line 37: "may" should read --map--;

line 39: "Ksm" should read --KSM--;

line 43: "FIG.1" should read --FIG.1A--;

line 44: "Ksm" should read --KSM--;

line 48: "Ksm" should read --KSM--;

line 52: "Ksm" should read --KSM--;

line 55: "pair" should read --pairs--;

line 56: "FIG.1" should read --FIG.1A--;

line 57: "Ksm" should read --KSM--;

UNITED STATES PATENT AND TRADEMARK OFFICE
CERTIFICATE OF CORRECTION

PATENT NO. : 4,904,599
DATED : February 27, 1990
INVENTOR(S) : Osaki et al.

It is certified that error appears in the above-identified patent and that said Letters Patent is hereby corrected as shown below:

Column 12, line 37, "may" should read --map-- line 61 "DMA" should read --DNA-- line 57, "Fig. 1" should read --Fig. 1A-- line 61, "Ksm" should read --KSM--;

line 66: "Ksm" should read --KSM--.

Signed and Sealed this

Twenty-third Day of June, 1992

Attest:

DOUGLAS B. COMER

*Attesting Officer*   Acting Commissioner of Patents and Trademarks